US006506704B1

(12) United States Patent
Bansleben et al.

(10) Patent No.: US 6,506,704 B1
(45) Date of Patent: Jan. 14, 2003

(54) OLEFIN POLYMERIZATION CATALYSTS AND PROCESSES FOR MAKING AND USING SAME

(75) Inventors: Donald Albert Bansleben, Columbia, MD (US); Eric Francis Connor, Pasadena, CA (US); Robert Howard Grubbs, South Pasadena, CA (US); Jason Ivan Henderson, Pasadena, CA (US); Todd Ross Younkin, Pasadena, CA (US)

(73) Assignee: Cryovac, Inc., Duncan, SC (US)

( * ) Notice: Subject to any disclaimer, the term of this patent is extended or adjusted under 35 U.S.C. 154(b) by 0 days.

(21) Appl. No.: 09/274,378

(22) Filed: Mar. 23, 1999

(51) Int. Cl.$^7$ ................................................ B01J 31/00
(52) U.S. Cl. ........................ 502/155; 502/162; 502/167; 502/168; 502/172; 502/156
(58) Field of Search ................................. 502/162, 167, 502/168, 172, 155, 156

(56) References Cited

U.S. PATENT DOCUMENTS

| | | | |
|---|---|---|---|
| 3,635,937 A | 1/1972 | Bauer et al. | 260/94.9 C |
| 3,644,563 A | 2/1972 | Bauer et al. | 260/683.15 |
| 3,647,915 A | 3/1972 | Bauer et al. | 260/683.15 D |
| 3,686,159 A | 8/1972 | Bauer et al. | 260/94.9 C |
| 4,293,502 A | 10/1981 | Beach et al. | 260/439 R |
| 4,293,727 A | 10/1981 | Beach et al. | 585/526 |
| 4,301,318 A | 11/1981 | Beach et al. | 585/526 |
| 4,310,716 A | 1/1982 | Beach et al. | 585/526 |
| 4,382,153 A | 5/1983 | Beach et al. | 585/526 |
| 4,533,651 A | 8/1985 | Masters et al. | |
| 4,537,982 A | 8/1985 | Starzewski et al. | 556/22 |
| 5,210,360 A | 5/1993 | Wu | |
| 5,539,124 A | 7/1996 | Etherton et al. | |
| 5,557,023 A | 9/1996 | Somogyvari et al. | 585/513 |
| 5,714,556 A | 2/1998 | Johnson et al. | 526/135 |
| 5,852,145 A | 12/1998 | McLain et al. | 526/133 |
| 6,174,975 B1 * | 1/2001 | Johnson et al. | 526/172 |
| 6,197,714 B1 * | 3/2001 | Bansleben et al. | 502/172 |
| 6,197,715 B1 * | 3/2001 | Bansleben et al. | 502/172 |
| 6,303,720 B1 * | 10/2001 | Mackenzie et al. | 502/168 |
| 6,309,997 B1 * | 10/2001 | Fujita et al. | 502/167 |
| 6,313,243 B1 * | 11/2001 | Tohi et al. | 502/168 |
| 2001/0025007 A1 * | 9/2001 | Ponasik, Jr. et al. | 502/167 |

FOREIGN PATENT DOCUMENTS

| | | |
|---|---|---|
| WO | 9623010 | 1/1996 |
| WO | WO 97/48736 | * 12/1997 |
| WO | 9830609 | 7/1998 |
| WO | 98/42664 | 10/1998 |
| WO | 9912981 | 3/1999 |

OTHER PUBLICATIONS

Klein, Hans–Friedrich et al: "Methylnickel compounds containing trimethylphosphine and salicylaldiminato(N:O) ligands", Inorganica Chimica Acta, (1996), 248(1), pp. 111–114.

Younkin, Todd R. et al: "Neutral, single–component nickel (II) polyolefin catalysts that tolerate heteroatoms", Science (Washington, D.C.) (2000), 287(5452), pp., 460–462.

* cited by examiner

Primary Examiner—Mark L. Bell
Assistant Examiner—J. Pasterczyk

(57) ABSTRACT

A process for forming neutral late transition metal chelates useful as polymerization catalysts comprising contacting a bidentate ligand forming compound that is free of electron-withdrawing groups with a di(tertiary amine) late transition metal reagent in the presence of an inert liquid, an olefinic monomer or a polar liquid selected from nitrites, ethers, aromatic heterocyclic amines, alcohols, nitroalkanes, nitroaromatics or mixtures thereof. The process provides a solid product or a solution of a storage stable transition metal bidentate ligand containing catalyst product which remains active for an extended storage period. Alternately, the present process can be conducted in situ in a polymerization zone of olefinic polymerization.

22 Claims, No Drawings

OLEFIN POLYMERIZATION CATALYSTS AND PROCESSES FOR MAKING AND USING SAME

This invention was made with United States Government support under Contract No. 70NANB5H1136 awarded by the U.S. Department of Commerce's National Institute of Standards and Technology. The United States has certain rights in the invention.

BACKGROUND INFORMATION

1. Field of the Invention

The subject invention is directed to an improved method of forming a non-ionic (neutral) late transition metal chelate which is useful as a catalyst for the polymerization of olefins. The improved method provides novel chelates which exhibit high catalytic activity for olefin polymerization.

2. Background of the Invention

The polyolefin industry has relied on various catalyst and free radical initiator systems to polymerize ethylene and other non-polar 1-olefins. Such polymerization has been accomplished using organometallic Ziegler-Natta coordination type catalysts, chromium catalysts, certain early transition metal catalysts, as well as free-radical type initiators. It is well known that these catalysts are highly susceptible to a range of substances which poison or deactivate their catalytic activity. For example, it is known that even trace amounts of oxygen, carbon monoxide, water, or organic substances having oxygen donor groups cause deactivation of transition metal catalysts. When such substances are present one is usually restricted to free radical initiator systems.

Two recent publications, WO 98/42664 and WO 98/42665, disclose certain novel late transition metal salicylaldimine and pyrrolaldimine chelates that can act as single-site olefin polymerization catalysts which are not oxophilic. Thus, these chelates may be used to catalyze the polymerization of ethylene alone or with other 1-olefins or cycloolefins including those having oxygen atom-containing functional groups (e.g., ether, ester, carbonyl, carboxyl, or hydroxy groups). Further, these chelates provide good catalytic activity and are resistant to being poisoned even when used in the presence of moisture or organic compounds having oxygen atom containing groups.

The disclosed process for forming these catalyst chelates includes initially deprotonating the appropriate ligand using a lithium alkyl or an alkali metal hydride followed by chelation of the deprotonated (anionic) ligand with a late transition metal coordination compound. Both of these process steps use reagents which are difficult to handle. Further, the process produces a late transition metal chelate which contains an ancillary ligand, such a triphenylphosphine, associated with the transition metal atom. It is believed that such ligand must be dissociated from the chelate to provide catalytic polymerization activity. Normally, such ligands do not completely dissociate; thus, chelates having such ancillary ligands exhibit catalytic activity which is lower than expected. Certain adjunct agents are taught to assist in ancillary ligand dissociation.

Another recent PCT publication, WO 98/30609, discloses a number of late transition metal chelates as being useful as olefin polymerization catalysts. These chelates may also contain inert functional groups, such as electron withdrawing groups, as part the chelate structure. The resultant chelate comprises a ligand group which may be a neutral bidentate ligand or a mono-anionic bidentate ligand associated with the metal atom of the chelate. In many instances the chelate exists in dimer form. Synthesis of these chelates is taught to be accomplished by protonation of suitable nickel(0) or nickel(II) precursors by a neutral ligand, preferably in the presence of phosphine or allyl ligand sponges such as copper chloride, triphenyl borane or the like.

The foregoing methods of forming non-ionic, bidentate late transition metal chelates provide products which exhibit only low or moderate catalytic activity. It would be highly desirable to have a process which is capable of forming non-ionic late transition metal chelates which are free of slow-to-dissociate ancillary ligand. Further, it would also be highly desirable to have a process which provides non-ionic late transition metal chelates which are storage stable. Still further, it would be highly desirable to have a process which provides non-ionic late transition metal chelates which exhibit high catalytic activity and extended polymerization life. It would also be highly desirable to provide a process for the polymerization of olefins where the catalyst is a highly active late transition metal chelate, where the chelate can be formed in situ in the polymerization media, and where the chelate is not poisoned by the presence of oxygenated compounds.

The present invention is directed to a process of forming non-ionic late transition metal chelates which have high catalytic activity for olefin polymerization. The present process does not require a metal alkyl- or metal hydride-assisted deprotonation of the ligand and produces chelates which are free of an associated (tightly bound) ligand entity. Further, one embodiment of the present process produces storage stable chelates. The present invention also provides a method of polymerization of 1-olefins alone or with functionalized olefins or cyclic olefins wherein the highly active catalyst is formed in situ in the polymerization medium. The process of the present invention eliminates the need for forming a mono-anionic form of the bidentate ligand and association of the resultant chelate with a labile phosphine or allyl type ligand, as preferred by prior processes.

SUMMARY OF THE INVENTION

The present process provides a highly active olefin polymerization catalyst including a neutral late transition metal chelate and involves contacting a dialkyl transition metal(II) diamine complex with a bidentate chelating ligand which is free of electron withdrawing groups and has certain sterically bulky substituents. Preferably, the ligand and dialkyl transition metal(II) diamine complex reagent are contacted in the presence of an aprotic polar liquid to provide a storage stable solid catalyst product. Alternatively, the chelate can be formed in situ and used as a polymerization catalyst.

DETAILED DESCRIPTION OF ILLUSTRATIVE EMBODIMENTS

The present invention is directed to a method of forming certain neutral, bidentate late transition metal chelates which remain stable during storage prior to use and to the storage stable chelates. The present invention is further directed to the formation of the chelates in situ and directly used as a polymerization catalyst.

The following terms are defined herein below to aid in providing a clear teaching of the present invention:

(A) "Hydrocarbyl" group refers to a univalent organic group composed of hydrogen and carbon. If not otherwise stated, it is preferred that said hydrocarbyl group contain from 1 to 40 carbon atoms.

(B) "Hydrocarbylene" group refers to a divalent organic group composed of hydrogen and carbon. If not otherwise stated, said hydrocarbylene group may include aliphatic, aromatic and mixed aliphatic/aromatic groups.

(C) "Hydrocarbyloxy" or "oxyhydrocarbyl" group refers to a univalent organic group composed of hydrogen, oxygen and carbon wherein the oxygen may be in the form of one or more ether oxygen, ester oxygen, ketone, aldehyde or carboxylic acid group(s) or mixtures thereof.

(D) "Hydrocarbyloxyene" or "oxyhydrocarbylene" refer to a divalent organic group composed of hydrogen, oxygen and carbon atoms wherein the oxygen atom may be in the form of an ether oxygen, ester oxygen, ketone, aldehyde or carboxylic acid group(s) or mixtures thereof.

(E) "Functional group" refers to ester, alcohol, carboxylic acid, halogen, primary, secondary and tertiary amine, aldehyde, ketone, hydroxyl nitro, and sulfonyl groups.

(F) "Aryl" and "arylene" refer, respectively, to a monovalent and divalent carbocyclic aromatic ring which may consist of one or a plurality of rings (fused or non-fused).

(G) "Substituted" refers to an aryl or arylene group having one or more groups which do not interfere with the synthesis of the compound or the polymerization process for which the compound is contemplated wherein said one or more groups may be a hydrocarbyl, hydrocarbylene, oxyhydrocarbyl, oxyhydrocarbylene, inert functional group or the like.

(H) "Polymerization Unit" refers to a unit of a polymer derived from a monomer used in the polymerization reaction. For example, the phrase "alpha-olefin polymerization units" refers to a unit in, for example, an alpha-olefin/vinyl aromatic copolymer, the polymerization unit being that residue which is derived from the alpha-olefin monomer after it reacts to become a component of the polymer chain.

(I) "Polyolefin" refers to any polymerization olefin, which can be linear, branched, cyclic, aliphatic, aromatic, substituted, or unsubstituted. More specifically, including in the term polyolefin are homopolymers of olefins, copolymers of olefins, copolymers of an olefin and a non-olefinic comonomer copolymerization with the olefin, such as vinyl monomers, modified polymers thereof, and the like. Specific examples include polypropylene homopolymers polyethylene homopolymers, poly-butene, propylene/alpha-olefin copolymers, ethylene/alpha-olefin copolymers, butene/alpha-olefin copolymers, ethylene/vinyl acetate copolymers, ethylene/ethyl acrylate copolymers, ethylene/butyl acrylate copolymers, ethylene/methyl acrylate copolymers, ethylene/acrylic acid copolymers, ethylene/methacrylic acid copolymers, modified polyolefin resins, ionomer resins, polymethylpentene, etc. and the like.

The catalysts formed by the process of the present invention are late transition metal chelates wherein the metal is chelated with a bidentate ligand represented by the generic formulae:

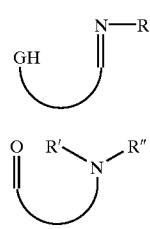

(I)

(II)

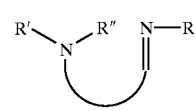

(III)

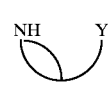

(IV)

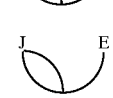

(V)

wherein

R represents a $C_4$–$C_{24}$ (preferably $C_4$–$C_{12}$) hydrocarbyl such as a $C_4$–$C_{12}$ alkyl group (e.g., butyl, pentyl, hexyl, heptyl and the like and all isomers thereof); a cycloalkyl such as cyclopentyl, cyclohexyl, adamantyl and the like; an aryl such as phenyl, biphenyl, naphthyl, anthracenyl, phenanthrenyl, m-terphenyl, terphenyl and the like; an aralkyl such as triphenylmethyl and the like; a substituted aryl having at least one position (preferably the ortho position(s)) of the aromatic group (preferably phenyl) substituted with a $C_1$–$C_{12}$ alkyl or a fused or unfused aryl group or an oxyhydrocarbylene group. It is especially preferred that R be a sterically bulky group such as an aryl or substituted aryl or aralkyl group as described above, particularly 2,6-diisopropylphenyl, anthracenyl, terphenyl, m-terphenyl, trityl, and the like;

each R' and R" independently is selected from hydrogen or an R group, as stated above, provided at least one of the R' and R" groups is a hydrogen, preferably R' is a hydrogen and R" is an R group;

G represents an oxygen or sulfur atom;

E represents an OH, SH, or NHR group;

J represents —O— or —S— as part of a ring structure;

Y represents an OR, SR, or NRR group where R is defined as above, preferably a sterically bulky hydrocarbyl group; and U represents a hydrocarbylene group which may comprise arylene, arylalkylene, alkarylene, cycloalkylene and/or alkylene group or a mixture thereof and wherein said groups may have carbon-carbon single covalent bonds only or combined with non-aromatic or aromatic carbon-carbon ethylenic double bonds within the hydrocarbylene structure.

For the ligand to be suitable to form a storage stable catalyst according to the present process, it must be free of electron withdrawing groups such as nitro, halo (chloro, bromo, etc.) sulfonate, carboxylate, perfluoroalkyl, sulfonyl and the like. Unexpectedly, when the present catalyst chelate is formed by the process described herein using a bidentate ligand reagent which is free of electron withdrawing groups and has sterically bulky groups (e.g., aryl, substituted aryl, aralkyl or highly branched $C_4$–$C_{24}$ alkyl), one is able to form a storage stable catalyst material having enhanced catalytic activity. The catalysts of the present invention retain high catalytic activity of at least about $10^5$ g polymer/mol cat/hr, with activities of from about $10^5$ to about $10^7$ g polymer/mol cat/hr and higher being readily observed.

Specific examples of ligands found useful in the present invention are given below.

(VI) 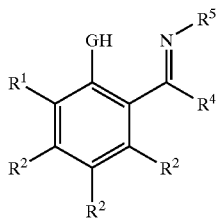

(VII) 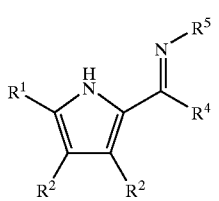

(VIII) 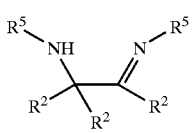

(IX) 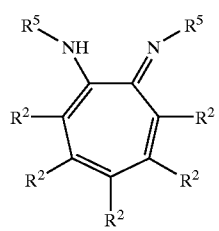

(X) 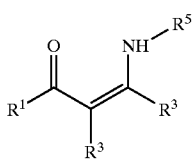

(XI) 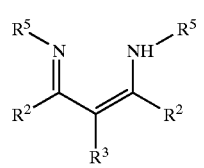

(XII) 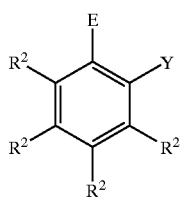

-continued (XIII) 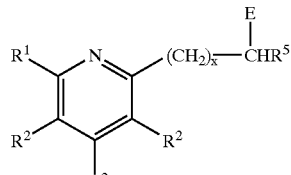

(XIV) 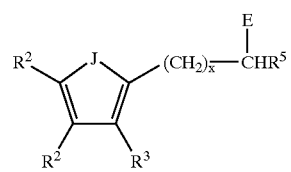

(XV) 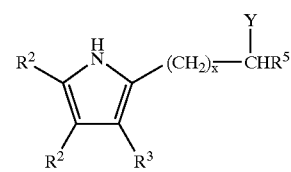

wherein
  each $R^1$ independently is a $C_4$–$C_{24}$ hydrocarbyl, a substituted $C_4$–$C_{24}$ hydrocarbyl which preferably is sterically bulky (e.g., an aryl, substituted aryl, aralkyl or a branched alkyl), or an $R^1$ group with an $R^2$ or $R^3$ group on a vicinal carbon together form a hydrocarbylene ring;
  each $R^2$ independently is a hydrogen, $C_1$–$C_{24}$ hydrocarbyl, substituted $C_1$–$C_{24}$ hydrocarbyl, an inert (non-electron withdrawing) functional group, or any two $R^2$ groups together or an $R^2$ group with an $R^1$ or $R^3$ which are on vicinal carbon atoms can form a hydrocarbylene ring;
  each $R^3$ independently is a $C_1$–$C_{24}$ hydrocarbyl, substituted $C_1$–$C_{24}$ hydrocarbyl, an inert functional group, or an $R^3$ group with an $R^1$ or $R^2$ which are on vicinal carbon atoms can form a hydrocarbylene ring;
  each $R^4$ independently is a hydrogen atom, hydrocarbyl, or substituted hydrocarbyl;
  each $R^5$ independently is a sterically bulky $C_6$–$C_{24}$ hydrocarbyl or a sterically bulky $C_6$–$C_{24}$ substituted hydrocarbyl, preferably an aryl, aralkyl or a $C_1$–$C_{12}$ hydrocarbyl substituted aryl; and
  G, E, J and Y are the same as defined as above.

Examples of hydrocarbyl and substituted hydrocarbyl groups are $C_4$–$C_{24}$ alkyl such as butyl, pentyl, hexyl, octyl, decyl, dodecyl, and the like and all isomers thereof; alkenyl groups such as 3-butenyl and the like; aryl such as phenyl, biphenyl, naphthyl, anthracenyl, terphenyl (all isomers), phenanthrenyl, and the like; alkaryl such as toluyl and the like; aralkyl such as trityl(triphenylmethyl), 4-(ethenylphenyl)diphenylmethyl and the like; and said hydrocarbyl groups having one or more substitution groups selected from $C_1$–$C_{12}$ alkyl, $C_1$–$C_{12}$ alkenyl, or a hydrocarbyl terminated oxyhydrocarbylene group —(BO)$_n$R wherein each B independently represents a $C_1$–$C_4$ (preferably $C_2$–$C_3$) alkylene group or an arylene group and R represents a $C_1$–$C_{11}$ (preferably $C_1$–$C_3$) hydrocarbyl group such as an alkyl, unsubstituted or substituted aryl and n is an integer of 1–4.

To form a storage stable catalyst of the present invention, $R^5$ of the above ligands and of the resulting catalyst chelate must be sterically bulky groups selected from aryl, such as for example phenyl, biphenyl, naphthyl, anthracenyl, phenanthrenyl, terphenyl (all isomers) and the like; aralkyl such as toluyl and the like; alkaryl such as trityl, 4-(ethenylphenyl)diphenylmethyl and the like and substituted aryl groups wherein the substitution is selected from $C_1$–$C_{12}$ alkyl, $C_1$–$C_{12}$ alkenyl or a hydrocarbyl terminated oxyhydrocarbylene group —$(BO)_nR$ as defined above. Further, for the resultant catalyst chelate formed according to the present invention to be storage stable, $R^1$ must be a sterically bulky group selected from a $C_4$–$C_{24}$ branched alkyl such as, for example, t-butyl, 1,1-dimethyl propyl, 1-methyl-1-ethyl propyl, 1,1-diethyl propyl and the like; or an $R^5$ group. Preferably, $R^1$ and $R^5$ both are sterically bulky groups independently selected from aryl, aralkyl, alkaryl, and substituted aryl groups as described above with respect to $R^5$.

The ligand is contacted with di(tertiary amine) late transition metal reagent represented by the formula

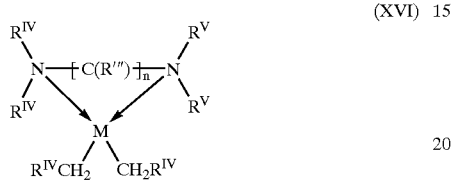
(XVI)

wherein
- $R'''$ represents hydrogen (preferable) or a $C_1$–$C_5$ alkyl or substituted alkyl;
- $R^{IV}$ and $R^V$ each independently represents a hydrocarbyl, such as a $C_1$–$C_{10}$ alkyl, preferably $C_1$–$C_3$ alkyl and most preferably a methyl group or each $R^{IV}$ together and each $R^V$ together represents a hydrocarbylene group which may be aromatic or non-aromatic;
- $R^{VI}$ each independently represents hydrogen, aryl, $SiOR_3$ or a tri($C_1$–$C_{12}$ hydrocarbyl)methyl group, —CRRR, wherein each R is a substituent independently selected from a $C_1$–$C_{12}$ hydrocarbyl as defined above, with hydrogen being preferred;
- M represents a Group VIII transition metal selected from Fe, Co, Ni, Ru, Rh, Pd, Os, Ir or Pt in the +2 oxidation state, preferably Ni or Pd and most preferably Ni; and
- n represents an integer of from 0 to 3, and preferably n is an integer of from 1 to 3, when each $R^{IV}$ and each $R^V$ is a hydrocarbyl with the proviso that n preferably is 0 when both $R^{IV}$ and both $R^V$ are hydrocarbylene groups.

The above reagents can be readily formed. For example, the nickel(II) chelate of tetramethylethylenediamine is formed by first contacting tetramethylethylenediamine with nickel(II) acetylacetonate in an inert hydrocarbon solvent, such as pentane, heptane, or the like. The nickel acetylacetonate product then is alkylated in an inert aprotic solvent such as diethylether, tetrahydrofuran, or the like at about –30° C. with dimethyl magnesium tetramethylethylenediamine to provide a mixture of the desired (insoluble) ditertiary amine late transition metal agent [e.g. dimethyl nickel (II) tetramethylethylenediamine] and a soluble magnesium by-product. The desired metallation agent can be separated from the by-product by decanting the solvent which contains the soluble by-product and several washes of the insoluble (tmeda) Ni(CH$_3$)$_2$ with fresh polar aprotic solvent at –30° C. The specific liquid to use depends on the solubility parameters of the reagent and by-product and can be readily determined by routine screening.

Preferred agents include late transition metal agents formed with tetramethylethylenediamine, and preferred metals include Ni(II) or Pd(II), most preferably Ni(II).

The present process includes contacting the bidentate chelating ligand described above with a late transition metal agent described above. The ligand and late transition metal agent are contacted in an inert liquid, preferably a polar aprotic liquid such as a nitrile, ether, aromatic heterocyclic amine and the like, as fully described below. The ligand and metal agent may be contacted at any temperature which does not cause degradation of the reactants or the chelate product, such as from between about –20° C. to about 70° C. or higher, preferably from about 0° C. to about 50° C.

In one embodiment of the subject invention, one forms a catalytically active, storage stable chelate product. (The term "storage stable" refers herein and in the appended claims to a chelate product which can be isolated, does not dimerize or otherwise degrade and can be stored for periods of up to at least about 3 months, more generally up to at least about 6 months, while retaining its catalytic activity prior to utilization.) The process of forming a storage stable catalyst requires the ligand to be free of electron withdrawing groups such as, for example, nitro, halo (chloro, bromo, and the like), sulfonate, sulfonyl ester, carboxylate, perfluoroalkyl, and the like. Further, the present process requires a ligand which has sterically bulky groups thereon especially at the $R^1$ and $R^5$ positions of the ligand and resultant chelate.

The chelating ligand and the late transition metal agent are contacted in the presence of an aprotic polar liquid "Sol" to provide a metal chelate product which has enhanced catalytic polymerization activity and maintains such activity while being storage stable. Examples of useful polar liquids S include nitrites (preferred) as, for example, acetonitrile (most preferred), propionitrile, butyralnitrile, benzonitrile, and the like; an ether as, for example, tetrahydrofuran, glyme, diglyme and the like; or an aromatic heterocyclic amine as, for example, pyridine, lutidine and the like. The aprotic liquid should be present in the reaction zone in at least a slight molar excess quantity based on the molar quantity of transition metal (e.g., at least 1.01 moles per mole of transition metal, more preferably at least 1.1 moles per mole of transition metal). The aprotic liquid can be used as some or all of the solvent of the reaction mixture.

A common identifying feature of the desired catalyst compound is the methyl NMR signal associated with the metal $CH_3$ bond of the present chelates at about –0.8 ppm or lower (depending on the identity of "Sol").

The above process of contacting a bidentate ligand free of electron withdrawing groups with a late transition metal agent in the presence of an aprotic polar solvent, as described above, produces a chelate product represented by the following formulae:

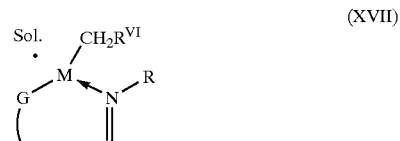
(XVII)

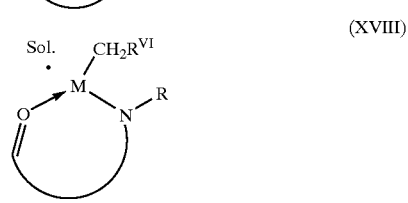
(XVIII)

-continued

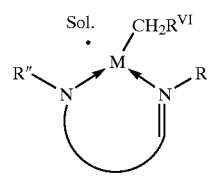 (XIX)

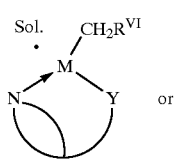 (XX)

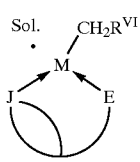 (XXI)

wherein

R, R", G, E, J, Y, and ∪ correspond to the precursor ligand moiety of I to V described above which is used to form said chelate and R and R" of the resultant chelate are thus each independently selected from a $C_4$–$C_{24}$ hydrocarbyl selected from cycloalkyl, aryl, substituted aryl wherein the substitution is selected from a $C_1$–$C_4$ alkyl, an unfused or fused aryl or is a hydrocarbyl terminated oxyhydrocarbylene group;

$R^{VI}$ each independently represents hydrogen, aryl, $SiOR_3$ or a tri($C_1$–$C_{12}$ hydrocarbyl)methyl group, —CRRR, wherein each R is a substituent independently selected from a $C_1$–$C_{12}$ hydrocarbyl as defined above, with hydrogen being preferred;

M represents a late transition metal ion, that is a metal atom of Group IV or VIII transition metals, preferably selected from Fe, Co, Ni, Ru, Rh, Pd, Os, Ir or Pt in the +2 oxidation state, preferably iron, cobalt, nickel or palladium and still more preferably nickel or palladium with nickel being the most preferred; and Sol represents an aprotic solvent molecule (described above) in association with the chelate.

The chelates XVII, XVIII, XIX, XX and XXI are formed from the ligands I, II, III, IV or V, respectively.

Examples of such neutral bidentate late transition metal chelates are given below (and correspond to the ligand precursors VI to XV and their respective groups described above):

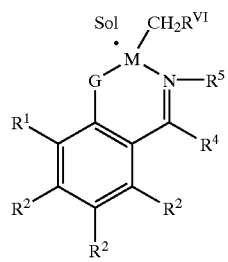 (VIa)

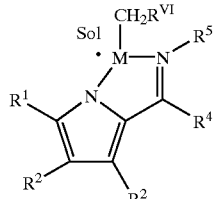 (VIIa)

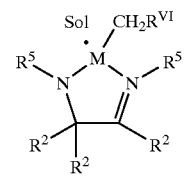 (VIIIa)

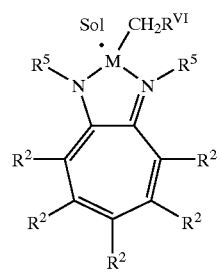 (IXa)

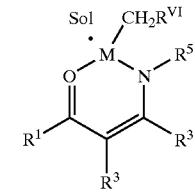 (Xa)

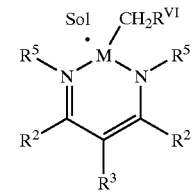 (XIa)

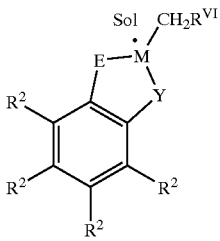 (XIIa)

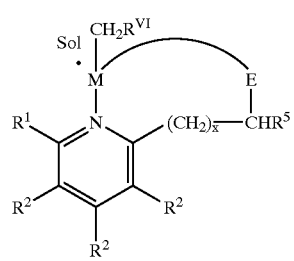 (XIIIa)

-continued

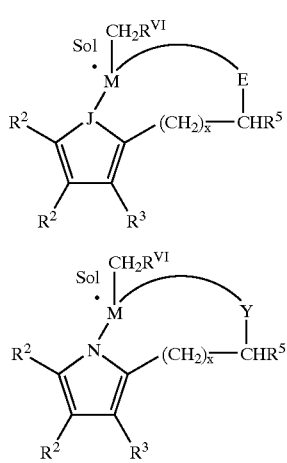
(XIVa)

(XVa)

As stated above, the chelate product of the present process can be isolated, stored and used as a catalyst for the polymerization of a 1-olefin such as ethylene, alone, or in conjunction with a functionalized olefin or cyclic olefin, such as those disclosed in WO 98/42664 and WO 98/42665, the teachings of which are incorporated herein in their entirety by reference.

It is believed although not meant to be a limitation of the present invention, as described herein or defined in the claims appended hereto, that the chelate obtained by the process of the present invention wherein the precursor bidentate ligand is free of electron withdrawing groups, the bidentate ligand contains sterically bulky groups, and the bidentate ligand and metal agent are contacted to form the chelate in the presence of an aprotic polar liquid provide a neutral chelate which is free of an ancillary ligand group, such as triphenylphosphine or allyl, associated with the transition metal of the chelate. Although such ancillary ligand can disassociate from the metal when in the presence of a pi-bond olefin, such dissociation is not complete or rapid. The lack of substantially complete and rapid dissociation of an ancillary ligand from prior known chelates provide a catalytic activity which is substantially inferior to that of the chelate products presently produced wherein an aprotic solvent molecule "S" which is highly disassociative is a part of the chelate product.

A second embodiment of the subject invention is directed to a process of forming the neutral chelate in-situ in a polymerization process medium. In this embodiment the precursor ligand I–V and the late transition metal agent XVI described above are introduced into the polymerization zone to initiate and catalyze the polymerization of an olefin or of the copolymerization of an olefin and a functionalized olefin or cyclic olefin.

The polymerization may be carried out at conventional temperatures (e.g., about −100° C. to about +200° C., preferably from −20° C. to +100° C., and most preferably between 0° C. and 70° C.). All ranges of temperatures being covered by this teaching. The pressure of the polymerization may be from atmospheric pressure to about 100 MPa or more, with all ranges of pressure being covered by this teaching. The polymerization is preferably carried out in a liquid which also acts as a liquid medium in which the ligand and the transition metal agent contact each other. The liquid may be (i) the monomer(s), per se or (ii) any organic compound (preferably hydrocarbon) which is liquid under the polymerization conditions and is inert toward the monomers, polymer, ligand, metal agent, and resultant chelate.

In this second embodiment, an aprotic polar liquid may be present. If present, the aprotic polar liquid preferably is an ether as, for example, diethylether, glyme, diglyme, tetrahydrofuran and the like; a nitrile as, for example, acetonitrile, propionitrile, butyralnitrile, benzonitrile or the like; an aldehyde or ketone, such as acetone, propanone, cyclohexanone, acetaldehyde, benzaldehyde and the like; an alcohol such as methanol, ethanol, propanol, butanol and the like; organic esters such as ethyl acetate, propylacetate, ethyl laurate and the like; nitroalkanes and nitroaromatics such as nitropropane, nitrobenzene and the like; as well as mixtures thereof.

Further, when forming the catalyst chelate in situ in the polymerization zone, the ligand and, therefore, the resultant chelate catalyst formed in situ may have an electron withdrawing group as part of the molecule. When such groups are present, they may be a substituent moiety of a hydrocarbyl of $R^1$, $R^2$, $R^3$, $R^4$ or $R^5$ and preferably of the hydrocarbyl of $R^1$ and/or $R^5$ sterically bulky groups selected from $C_4$–$C_{24}$ hydrocarbyl such as an aryl, substituted aryl or a highly branched alkyl group. When such groups are present as part of ligand VI, the position para with respect to the G moiety preferably is an electron withdrawing group.

One of the advantages of this second embodiment is that the present chelate catalyst can be formed in-situ in the polymerization media from easy to handle reagents. Further, the polymerization media need not contain a "sponge" for phosphine or allyl-type ancillary ligand, as is commonly used with prior taught bidentate chelate catalysts. Finally, the present process provides a catalyst which exhibits enhanced activity over that provided for by prior modes of formation.

This invention also concerns processes for making polymers and copolymers that includes contacting the subject catalyst composition with one or more selected olefins or cycloolefins, alone or optionally with a functional 1-olefin such as a carboxylic acid of the formula $CH_2=CH(CH_2)_m COOH$, a carboxylic acid ester of the formula $CH_2=CH(CH_2)_m CO_2 R^4$ or $CH_2=CHOCOR^{14}$, an alkyl vinyl ether of the formula $CH_2=CH(CH_2)_m OR^{14}$, vinyl ketones of the formula $CH_2=CH(CH_2)_m C(O)R^{14}$, a vinyl alcohol of the formula $CH_2=CH(CH_2)_m OH$, or a vinyl amine of the formula $CH_2=CH(CH_2)_m NR^{14}_2$, wherein m is an integer of 0 to 10 and $R^{14}$ is a $C_1$–$C_{10}$ hydrocarbyl group, aryl or substituted aryl group (preferably methyl); a functional cycloolefin, such as an exo-functionalized norbornene wherein the functional group is an ester, alcohol, carboxylic acid, halogen atom, tertiary amine group or the like; unsaturated dicarboxylic acid anhydride or carbon monoxide or the like; and other selected monomers such as vinyl halides. The "polymerization process" described herein (and the polymers made therefrom) is defined as a process which produces a polymer with a weight average molecular weight ($M_w$) of at least about 10,000.

Catalytic polymerization according to the present invention can be carried out by contacting one or more selected olefins or cycloolefins alone or optionally with a functional olefin or cycloolefin monomer, as described above with a neutral catalyst chelate which has been previously formed according to the present invention or which is formed in-situ from one or more of the bidentate ligands described above and a transition metal reagent. When the polymerization process is carried out according to the second embodiment described herein, the ligand and reagent should be used in about 1:0.75 to 1:1.5 molar ratio. In a preferred embodiment of the present invention, the bidentate ligand is combined with a transition metal reagent in about a 1:1 to 1:1.05 molar ratio in the presence of olefin and/or cycloolefin alone or optionally with a functional olefin monomer. The catalyst thus formed in situ may further contain a Lewis base additive, such as ethers, esters, ketones, aldehydes, and the like.

With respect to all catalysts and precursor bidentate ligands described herein, $R^1$ and $R^5$ each is preferably independently a sterically bulky hydrocarbyl. In one form, $R^1$ and/or $R^5$ preferably are independently selected from a hydrocarbyl-terminated oxyhydrocarbylene containing group, as described above. Also, $R^1$ and $R^2$ can be taken together to provide a hydrocarbylene which forms a carbocyclic ring. It is preferred that $R^2$, $R^3$ and $R^4$ are hydrogen or methyl unless $R^2$ is, when taken together with $R^1$ or $R^3$, a $C_4$–$C_{10}$ carbocyclic group which may or may not be aromatic. Either or both $R^1$ and $R^5$ preferably are phenyl, biphenyl, terphenyl (all isomers included), naphthyl, anthracenyl, phenanthracenyl, trityl, vinyltrityl, 2,6-diisopropylphenyl, 2,6-dimethylphenyl, 2,6-diethylphenyl, 4-methylphenyl, 2-isopropyl-6-methylphenyl, 2,4,6-trimethylphenyl, 2-t-butylphenyl, 2-t-butyl-4-methylphenyl, or 2,6-diisopropyl-4-methylphenyl.

The structure of the bidentate ligand and the resultant chelate with which it is associated may influence the polymer microstructure, polymer yield, and polymer molecular weight. For example, as described above, $R^1$ and $R^5$ each preferably is a bulky aryl or substituted aryl group. Complexes with $R^1$ of this type generally produce higher molecular weight, higher polymer yield and more linear polymer product for any given set of conditions. The neutral chelate resulting from the present process is contacted, usually in the liquid phase, with an olefin such as ethylene alone or with another 1-olefin and/or 4-vinylcyclohexane, 4-vinylcyclohexene, cyclopentene, cyclobutene, substituted norbornene, or norbornene. The liquid phase may include a compound added just as a solvent and/or may include the monomer(s) itself and/or may comprise a Lewis base (especially an ether or nitrile compound) in the liquid phase at reaction conditions. The temperature at which the polymerization is carried out is from about –100° C. to about +200° C., preferably about –20° C. to about +100° C. and most preferably between about 0° C. and 70° C., with all substituent ranges of temperatures being covered by this teaching. The pressure at which the polymerization is carried out is not critical, with atmospheric pressure to about 100 MPa or more being a suitable range. The pressure may affect the yield, molecular weight and linearity of the polyolefin produced, with increased pressure and lower temperature providing more linear and higher molecular weight polymer product.

Preferred 1-olefins and cyclic olefins in the polymerization are one or more of ethylene, propylene, 1-butene, 1-hexene, 1-octene, 1-pentene, 1-tetradecene, norbornene, and cyclopentene, with ethylene, propylene, cyclopentene and norbornene being more preferred. Ethylene (alone as a monomer) is especially preferred.

The polymerization may be conducted in the presence of various liquids. The solvent in which the polymerization may be conducted can be selected from (i) the monomer(s), per se or (ii) any organic compound which is liquid under the reaction conditions and is substantially inert to the reactants and product, or (iii) a Lewis base additive (except water which, when used, should be present in limited amounts) which is liquid under the reaction conditions, or mixtures thereof. Particularly preferred additives are aprotic organic liquids or organic ethers, organic nitriles or mixtures thereof. The catalyst systems, monomer(s), and polymer may be soluble or insoluble in these liquids, but obviously these liquids preferably do not inhibit the desired polymerization. Suitable liquids include alkanes, cycloalkanes, halogenated hydrocarbons, ethers, and aromatic and halogenated aromatic hydrocarbons. Specific useful solvents include hexane, heptane, toluene, xylene, and benzene, methylene chloride, ethyl ether, chlorobenzene, dimethoxyethane, tetrahydrofuran and crown ethers.

The catalyst formed according to the present invention can facilitate the polymerization of one or more 1-olefin(s) with functional olefins such as those described above. Carbon monoxide unexpectedly has been found to be useful as a comonomer to form alternating copolymers with the various 1-olefins using the catalytic process of the present invention. The polymerization is carried out with both CO and the olefin simultaneously present in the process mixture, and in the presence of the present catalyst. Such polymerization is carried out under conditions described above. The presently derived catalyst has been unexpectedly found to be more tolerant to carbon monoxide and thereby achieves higher conversion of carbon monoxide into the resultant copolymer than prior taught catalyst compositions.

The neutral catalysts of the present invention, when previously formed according to the first embodiment described above, may be supported on a porous solid material (as opposed to just being added as a suspended solid or in solution), for instance on silica gel, zeolite, alumina, crosslinked organic polymers such as styrene-divinylbenzene copolymer, and the like. By supported is meant that the catalyst may simply be carried physically on the surface of the porous solid support, may be adsorbed, or may be carried by the support by other means.

The present catalyst has been found to be particularly suitable for use on a support and as a catalyst for gas phase polymerization processes. This is very useful as the present catalyst does not require the presence of an activator (co-catalyst) or adjunct agent.

In many of the polymerizations, certain general trends may occur, although for all of these trends there are exceptions. Pressure of the monomers (especially gaseous monomers such as ethylene) has an effect on the polymerizations in many instances. Higher pressure often reduces branching and extends polymer chain length, especially in ethylene containing polymers. Temperature also affects these polymerizations. Higher temperature usually increases branching and reduces molecular weight of the polymer product.

The resultant polymers formed according to the present invention, especially those of ethylene homo or copolymers may have varying degrees of branching in the polymer. Branching may be determined by NMR spectroscopy, and this analysis can determine the total number of branches, the branching distribution and, to some extent, the length of the branches. The amount of branching is usually expressed as the number of branches per 1000 of the total carbon atoms present in the polymer, with one exception. Methylene groups that are in an ester grouping, i.e., —$CO_2R$, or a ketone group, i.e., —C(O)R, are not counted as part of the 1000 carbons. For example, ethylene homopolymers have a branch content of about 0 to about 150 branches per 1000 carbon atoms, preferably about 5 to about 100 and most preferably about 2 to about 70 branches per 1000 carbon atoms. These branches do not include polymer end groups. Alternatively, branch content can be estimated from correlation of total branches as determined by NMR with polymer melting point as determined by differential scanning calorimetry.

The polymers formed by the present invention may be mixed with various additives normally added to elastomers and thermoplastics [see EPSE (below), vol. 14, p. 327–410] which teaching is incorporated herein by reference. For instance reinforcing, non-reinforcing and conductive fillers, such as carbon black, glass fiber, minerals such as silica, clay, mica and talc, glass spheres, barium sulfate, zinc oxide, carbon fiber, and aramid fiber or fibrids, may be used. Antioxidants, antiozonants, pigments, dyes, slip agents, antifog agents, antiblock agents, delusterants, or compounds to promote crosslinking may be added. Plasticizers such as various hydrocarbon oils may also be used.

The polymers formed by the present invention may be used for one or more of the applications listed below. In some cases a reference is given which discusses such uses for polymers in general. All of these references are hereby included by reference. For the references, "U" refers to W. Gerhartz, et al., Ed., Ullmann's Encyclopedia of Industrial Chemistry, 5th Ed. VCH refers to Verlagsgesellschaft mBH, Weinheim, for which the volume and page number are given, "ECT3" refers to the H. F. Mark et al., Ed., Kirk-Othmer Encyclopedia of Chemical Technology, 4th Ed., John Wiley & Sons, New York, "ECT4" refers to the J. I. Kroschwitz, et al., Ed., Kirk-Othmer Encyclopedia of Chemical Technology, 4th Ed., John Wiley & Sons, New York, for which the volume and page number are given. "EPST" refers to H. F. Mark et al., Ed., Encyclopedia of Polymer Science and Technology, 1st Ed., John Wiley & Sons, New York, for which the volume and page number are given, "EPSE" refers to H. F. Mark et al., Ed., Encyclopedia of Polymer Science and Engineering, 2nd Ed., John Wiley & Sons, New York, for which volume and page numbers are given, and "PM" refers to J. A. Brydson, Ed., Plastics Materials, 5th Ed., Butterworth-Heineman, Oxford, UK, 1989, and the page is given. In these uses, a polyethylene, polypropylene and a copolymer of ethylene and propylene are preferred.

1. The polyolefins herein are especially useful in blown film applications because of their particular rheological properties (EPSE, vol. 7, p. 88–106). These polymers preferably have some crystallinity.

2. The polymers are useful for blown or cast films or as sheet (see EPSE, vol. 7 p. 88–106; ECT4, vol. 11, p. 843–856; PM, p. 252 and p. 432ff). The films may be single layer or multilayer, the multilayer films may include other polymers, adhesives, etc. For packaging the films may be stretch-wrap, shrink-wrap or cling wrap and may also be heat sealable. The films are useful for many applications such as packaging foods or liquids, geomembranes and pond liners. These polymers also preferably have some crystallinity.

3. Extruded films or coextruded films may be formed from these polymers, and these films may be treated, for example by uniaxial or biaxial orientation after crosslinking by actinic radiation, especially electron beam irradiation. Such extruded films are useful for packaging of various sorts. The extruded films may also be laminated to other films using procedures known to those skilled in the art. The laminated films are also useful for packaging of various sorts.

4. The polymers, particularly if elastomeric, may be used as tougheners for other polyolefins such as polypropylene and polyethylene.

5. Tackifiers for low strength adhesives (U, vol. A1, p. 235–236) are a use for these polymers. Elastomers and/or relatively low molecular weight polymers are preferred.

6. An oil additive for smoke suppression in single-stroke gasoline engines is another use. Elastomeric polymers are preferred.

7. The polymers are useful as base resins for hot melt adhesives (U, vol. A1, p. 233–234), pressure sensitive adhesives (U, vol. A1, p. 235–236) or solvent applied adhesives. Thermoplastics are preferred for hot melt adhesives.

8. Base polymer for caulking of various kinds is another use. An elastomer is preferred. Lower molecular weight polymers are often used.

9. Wire insulation and jacketing may be made from any of the polyolefins (see EPSE, vol. 17, p. 828–842). In the case of elastomers it may be preferable to crosslink the polymer after the insulation or jacketing is formed, for example by a free radical process.

The following examples are provided for illustrative purposes only and are not meant to be a limitation on the scope of the invention. All parts and percentages are by weight unless otherwise indicated.

EXAMPLES

The general method used for synthesizing phosphine-free nickel(II) complexes involved the use of N,N,N',N'-tetramethylethylenediamine-(dimethyl)nickel(II) or (tmeda)Ni(CH$_3$)$_2$ as prepared by the method of W. Kaschube et al, J. Organomet. Chem., 355 (1988) 525–532. Reaction of this dialkylnickel(II) complex with various salicylaldimine bidentate ligands which were prepared previously using procedures described by C. Wang et al. in WO 98/42664 and Organometallics 1998, 17 (3149–3151) gave active single site catalysts for olefin polymerization. Unexpectedly, the resultant nickel(II) methyl complexes could only be isolated as storage-stable chelates when a Lewis base (e.g., acetonitrile, pyridine) was present during formation of the complex and electron-withdrawing groups (e.g., nitro, chloro) were absent from the salicylaldimine ligand. If electron-withdrawing substituents were present, then side-reactions such as formation of a bis-ligand complex occurred during attempts to isolate the complex.

Highly active olefin polymerization catalysts were also prepared in-situ by the addition of the protonated form of the salicylaldimine ligand to the (tmeda)Ni(CH$_3$)$_2$ reagent in an inert solvent followed by the addition of the desired olefin(s) (e.g., ethylene). In this instance, electron-withdrawing groups can be present as substituents on the salicylaldimine ring. Rapid polymerization which occurs in-situ is believed to prevent formation of lesser active forms (e.g., bis-ligand chelate or dimeric chelate) of the catalyst through side-reactions. Descriptive examples for the preparation of storage-stable and in-situ forms of neutral nickel(II) chelates of bidentate salicylaldimine ligands follow.

Storage-stable neutral nickel(II) chelates of general Formula VIa above were prepared according to the method just described. In each, M was Ni(II), $R^{VI}$ was H, G was O, each $R^2$ was H, $R^5$ was a 2,6-diisopropylphenyl group, and S was CH$_3$CN. The $R^1$ groups varied from (a) 9-anthracene, (b) phenyl, (c) thriphenylmethyl, to (d) 9-phenanthrene. Preparation of each of these is described below in Examples 1–4 respectively.

Examples 1

In a dry box, 9-anthracenylsalicylaldimine (0.58 g, 1.28 mmol) and (tmeda)Ni(CH$_3$)$_2$ (0.26 g, 1.29 mmol) were weighed and placed into a Schlenk tube, which then was placed on a vacuum line. Anhydrous acetonitrile (5 mL) was added to the flask by cannula. The reaction solution changed from an orange color to a red color within about 5 minutes and an evolution of bubbles (methane) was noted. After about 2 hours, crystals formed on the inside of the Schlenk tube. After about 8 hours, the dark red crystals were allowed to settle to the bottom of the flask, and the acetonitrile supernate was decanted.

The yield of red crystalline solid after drying was 0.51 g (68%). $^1$H NMR (CD$_2$Cl$_2$, 300 MHz, 25° C.): δ −1.41 (s, 3H, C$\underline{H}_3$Ni), 1.12, 1.33 (d, 6H, CH(C$\underline{H}_3$)$_2$), 1.86 (s, 3H, C$\underline{H}_3$CN), 3.83 (septet, 1H, C$\underline{H}$(CH$_3$)$_2$), 6.6–8.4 (m, 18H).

Example 2

To a solution of (tmeda)Ni(CH$_3$)$_2$ (0.259 g, 1.27 mmol) in acetonitrile (3 mL) in a Schlenk tube was added a solution of the Schiff base ligand (0.444 g, 1.44 mmol) in acetonitrile (3 mL). The solution color changed from yellow to a deep red color, and the evolution of bubbles was observed. The resulting mixture was stirred at room temperature for 6 hours before removing the acetonitrile by vacuum. The deep red solid was allowed to dry for 30 minutes.

The isolated yield of chelate product was 0.476 g (82%). A $^1$H NMR spectrum of the solid showed that two isomers were present in approximately equal amount (cis and trans for the methyl). The two isomers were assigned to tmeda filling the labile coordination site. The desired acetonitrile complex with a methyl shift at δ −1.25 ppm (CD$_3$CN, 300 MHz, 25° C.) was detected (10% of the total compound present). NMR spectroscopic data for the cis and trans tmeda isomers follows. $^1$H NMR (C$_6$D$_6$, 300 MHz, 25° C.): δ −1.25, −0.07 (d, 3H, C$\underline{H}_3$Ni), 1.07, 1.36 (d, 6H, CH(C$\underline{H}_3$)$_2$, one isomer), 1.1, 1.45 (d, 6H, CH(C$\underline{H}_3$)$_2$, 2$^{nd}$ isomer), 2.13, 2.33 (broad signals, (tmeda-η$^1$)Ni), 3.75 (septet for both isomers, 1H, C$\underline{H}$(CH$_3$)$_2$), 6.4–7.7 (m, 11H), 7.52, 8.00 (s, 1H, N=C$\underline{H}$). $^{13}$C NMR (CD$_3$CN, 300 MHz, 25° C.): δ −13.69 ppm ($\underline{C}$H$_3$Ni).

A desired amount of the above complex was dissolved in dry acetonitrile in a Schlenk tube and heated at 40° C. for 12 hours. Solvent was removed under vacuum. The isolated yield of dark red solid was 90%. Spectroscopic analysis of the product revealed that 90% of the desired acetonitrile complex was present. $^1$H NMR (CD$_3$CN, 300 MHz, 25° C.): δ −1.59 (s, 3H, CH$_3$Ni), 1.08, 1.37 (d, 6H, CH(C$\underline{H}_3$)$_2$), 2.46 (s, 3H, CH$_3$CN), 3.89 (septet, 1H, C$\underline{H}$(C$_3$)$_2$), 6.4–7.7 (m, 11H), 7.64 (s, 1H, N=C$\underline{H}$). $^{13}$C NMR (CD$_3$CN, 300 MHz, 25° C.): −14.93 ppm (C$\underline{H}_3$Ni).

Example 3

A. Preparation of Triphenylmethyl-Substituted Ligand

Triphenylmethyl alcohol (1.0 equiv.) and 3-aminophenol (1.3 equiv.) were added to a round bottom flask. Thereafter, acetic acid and concentrated HCl (4 mL for every 40 mL acetic acid) were added. The mixture was heated to reflux for 3 hours. At near reflux, the mixture became homogeneous. The mixture was cooled and the precipitated product was filtered and washed with chilled acetic acid. The product was then placed and water, and NaOH was added until the pH of the solution remained basic. Yield of 2-(triphenylmethyl)-3-aminophenol after filtration and drying was 85–95%. $^1$H NMR: δ 3.7 (broad, NH$_2$), 4.4 (broad, O$\underline{H}$), 6.15 (m), 6.8 (d), 7.3 (m). $^{13}$C NMR: δ 62.4, 104.3, 107.1, 123.6, 126.9, 128.1, 131.2, 131.6, 145.2, 148.0, 155.6.

This product was dissolved in a 50/50 solution of acetone and 50% H$_2$PO$_3$. The solution was chilled to 0° C. To keep the reaction temperature below 5° C., NaNO$_2$ (1.0 g, 2.0 equiv.) dissolved in water (10 mL) was added. The reaction was stirred for an additional 30 minutes. The (2-triphenylmethyl)phenol product was obtained by filtration and dried (yield 35–45%) prior to being recrystallized from hot acetic acid. (Proton NMR: δ 4.18 (broad), 6.79–6.92 (m), 7.1 (d), 7.18–7.4 (m). $^{13}$C NMR: 663.3, 118.2, 120.6, 127.0, 128.2, 129.3,130.8, 131.3, 133.5, 144.6, 154.9.).

The recrystallized product (1.0 equiv.) was dissolved in CH$_2$Cl$_2$/50% KOH/H$_2$O, and benzyltriethyl ammonium bromide (0.1 equiv.) was added as a phase transfer agent. To this two-phase mixture was added bromomethylmethylether (MOMBr). Reaction was allowed proceed for 30 minutes with stirring. The organic phase was separated, washed with water, brine, then dried with MgSO$_4$. Solvent was removed to yield the MOM-protected 2-(triphenylmethyl)phenol in near quantitative yield.

This product was dissolved in diethyl ether. The solution was chilled to −10° C. before n-butyl lithium (1.2 equiv.) was added dropwise. After a few minutes, a cream colored precipitate formed. The reaction was allowed to stir for 2 hours. To the reaction mixture was added dimethylformamide, DMF (1.5 equiv. with respect to phenol). The reaction mixture became homogeneous; however, over the course of stirring an additional 4 hours, a precipitate formed. To the reaction was added H$_2$O (1.5 equiv. with respect to the phenol) and stirring was maintained for another hour. The organic phase was separated, washed with water, brine, dried with MgSO$_4$ and dried under vacuum. Yield was 90–95%. (Proton NMR: an aldehyde peak was present at 10.4 ppm.) The product was purified by flash chromatography using 90/10 hexane/ethyl acetate to yield an off-white product which was used for the next step.

The MOM-protected 3-(triphenylmethyl)salicylaldehyde was dissolved in a 50/50 mixture of THF/6N HCl. The mixture was stirred for 4 hours prior to the addition of isopropyl alcohol and for another hour prior to the addition of diethyl ether. The organic phase was separated, washed with water, brine, dried over MgSO$_4$ and the solvent removed by vacuum. $^1$NMR showed a phenolic proton at about 13.5 ppm. The product was determined to be 3-(triphenylmethyl)salicylaldehyde.

To the product from the previous paragraph dissolved in benzene was added 2,6-diisopropylaniline (1.3 equiv.) with a catalytic amount of tosylic acid. The mixture was refluxed for 8 hours. Thereafter, solvent was removed, and the resultant oil was chromatographically separated with 90/10 hexanes/ethyl acetate. The product was an off-white solid isolated in 80–88% yield. $^1$H NMR: δ 1.06 (d), 2.82 (septet), 7.1–7.4 (m), 8.26 (s, inine NH).

B. Preparation of Storage-Stable Neutral Nickel(II) Chelate

In a dry box, the above-described Schiff base of salicylaldimine ligand having a trityl(triphenylmethyl) group in the 3-position (adjacent to the phenolic OH) (0.210 g, 0.401 mmol) was dissolved in benzene. Into another flask was added (tmeda)Ni(CH$_3$)$_2$ (0.10 g, 0.49 mmol). The flasks were removed from the dry box and placed on a vacuum line. To each flask was added anhydrous acetonitrile (3 mL). Both flasks were chilled to 0° C., and the ligand solution was added to the solution of (tmeda)Ni(CH$_3$)$_2$. A color change from yellow to orange was observed. The solution was allowed to stir for about 8 hours at 0° C. Thereafter, solvent was removed under vacuum.

The isolated yield of the desired chelate was 0.20 g (80%). $^1$H NMR (CD$_3$CN, 300 MHz, 25° C.): δ −1.68 (s, 3H, C$\underline{H}_3$Ni), 1.05, 1.33 (d, 6H, CH(C$\underline{H}_3$)$_2$), 2.32 (s, 3H, C$\underline{H}_3$CN), 3.83 (septet, 1H, C$\underline{H}$(CH$_3$)$_2$), 6.3–7.5 (m, 21H).

Example 4

Both the Schiff base of the salicylaldimine ligand (0.134 g, 0.294 mmol) and (tmeda)Ni(CH$_3$)$_2$ (0.091 g, 0.49 mmol) were weighed in separate flasks in a dry box. The flasks were removed from the dry box and placed on a vacuum line. To each flask was added anhydrous acetonitrile (3 mL). The nickel complex was chilled to −60° C., and the ligand solution was added to the other flask. The resulting clear red solution was allowed to warm to room temperature over a period of about an hour prior to the addition of anhydrous pyridine (0.5 mL) to the reaction mixture. Solvent was removed under reduced pressure, leaving an orange solid.

Yield of the isolated desired chelate was 0.146 g (82%). $^1$H NMR ($C_6D_6$, 300 MHz, 25° C.): δ −0.75 (s, 3H, $CH_3Ni$), 1.10, 1.12, 1.38, 1.54 (d, 6H, $CH(CH_3)_2$), 3.98–4.46 (septet, 1H, $CH(CH_3)_2$), 5.5–8.6 (m, 20H).

Example 5

Attempted Preparation of Storage-Stable Chelate Containing Electron-Withdrawing Substituents The 2,6-diisopropylaniline Schiff base of 3,5-dichlorosalicylaldehyde (0.20 g, 5.74 mmol) in anhydrous acetonitrile (3 mL) was added under a nitrogen atmosphere to a solution of $(tmeda)Ni(CH_3)_2$ (0.123 g, 6.00 mmol) in anhydrous acetonitrile (3 mL). A color change from yellow to deep red was observed. The resulting mixture was stirred for 2 days at ambient temperature. Dark red crystals formed during this time. Thereafter, solvent was decanted by cannula, and the remaining dark red crystals were placed under vacuum to dry.

The isolated yield of solid was 0.15 g. Proton NMR ($CD_2Cl_2$, 300 MHz, 25° C.): δ 1.22, 1.37 (d, 24 H, $CH(CH_3)_2$), 4.48 (septet, 4H, $CH(CH_3)_2$), 6.9–7.3 (m, 12H, aromatic). No significant methyl proton signal ($CH_3$—Ni) was observed. The NMR spectroscopic data of the dark red solid were consistent with a chelate having two of the dichloro-substituted Schiff base ligands coordinated to nickel.

Similar results were obtained when the ligand was the 2,6-diisopropylaniline Schiff base of 3-phenyl-5-nitrosalicylaldehyde.

The foregoing results demonstrate that a storage-stable neutral nickel(II) chelate could not be made from a ligand containing electron-withdrawing groups.

Example 6

Polymerization of Ethylene

A series of polymerizations were conducted as follows:

In an dry box, a 6-ounce (approximately 0.18 L) glass pressure bottle was charged with an appropriate amount of a neutral nickel(II) salicylaldimine complex of Examples 1 and 2 above. After the pressure bottle was removed from the dry box, degassed toluene (90 mL) was added by cannula. After the chelate dissolved, the bottle was pressurized to and maintained at about 0.79 MPa (100 psig) with ethylene.

Consumption of ethylene was rapid and caused a significant increase in the temperature of the polymerization mixture. The reaction was maintained for the times indicated below before being terminated by venting the reactor and adding the mixture to acidified methanol to precipitate the polymer product. The polyethylene product was filtered and dried under vacuum.

Table I below summarizes polymerization reactions of ethylene by the storage stable catalyst chelates from Examples 1 and 2. (Molecular weight averages were determined by GPC in trichlorobenzene at 135° C. and are relative to polyethylene numbers.).

TABLE I

| Chelate (Ex. no.) | Amt. of catalyst (μmol) | Reaction time (min) | Yield (g) | $M_w$ ($10^3$) | $M_w/M_n$ | Activity (kg PE/mol Ni/hr) |
|---|---|---|---|---|---|---|
| 1 | 60 | 60 | 21.4 | ND | | ND |
| 2 | 60 | 60 | 3.4 | 181 | 2.7 | 2,100 |
| 1 | 65 | 5 | 17.2 | | | 3190 |
| 1 | 59 | 5 | 20.4 | | | 4000 |
| 1 | 18 | 10 | 21.5 | | | 6400 |

ND = not determined

Example 7

Copolymerization of Ethylene and Carbon Monoxide

Two polymerizations were conducted in the following manner using the chelates of Example 2 and Example 3, respectively:

In a dry box, a glass pressure bottle was charged with 60 μmol of neutral nickel(II) salicylaldimine chelate. (The chelates from Examples 2 and 3 each were used.) After removal of the assembled bottle reactor from the dry box, degassed toluene (90 mL) was added by cannula.

After the complex had dissolved, the reaction vessel was pressurized to 0.17 MPa (10 psig) with carbon monoxide. Thereafter, the reactor immediately was pressurized to about 0.79 MPa (100 psig) with ethylene. Polymerization was carried out for 24 hours at a temperature of 50° C. After this time, the reactor was vented and the contents were poured into acidified methanol to precipitate the resulting white copolymer.

The ethylene-carbon monoxide (ECO) copolymer was filtered, dried under vacuum, and analyzed. An FTIR spectrum of the copolymer product showed a ketone carbonyl stretch (C=O) at 1691 cm$^{-1}$.

Yield of ECO copolymer using the chelate from Example 2 as catalyst was 1.6 g. Yield of ECO copolymer using the chelate from Example 3 as catalyst was 0.5 g.

Example 8

Heterogeneous-Phase Polymerization of Ethylene

In a dry box, a glass pressure bottle was charged with 60 μmol of the storage-stable, neutral nickel(II) chelate from Example 1. The assembled glass reaction vessel was removed from the dry box, and degassed toluene (0.5 mL) was added to solubilize the neutral nickel(II) chelate. After the complex had dissolved, the small volume of liquid was coated over the inside surface of the glass reactor.

The reactor was pressurized to 0.79 MPa (100 psig) with ethylene. Polymerization was carried out at that pressure for 24 hours. Polymer product formed as a white solid along the inside wall of the reactor. The polymer was collected from the wall and dried. The yield of polymer product recovered was 1.7 g.

The foregoing demonstrates that the storage-stable neutral nickel(II) chelate from Example 1 can be used as a catalyst in a gas phase olefin polymerization process.

Examples 9–12

In-Situ Formation of Neutral Nickel(II) Chelates

A series of polymerizations were conducted as follows:

Glass pressure bottles in a dry box were charged with appropriate amounts of the salicylaldimine ligands from Examples 1 and 2 as well as those identified in Table II below. For each of the chelates in the table below, G was O, M was Ni(II), $R^5$ was a 2,6-diisopropylphenyl group, S was $CH_3CN$, and $R^{VI}$ was H.

TABLE II

|    | $R^1$ | $R^2$ groups* |
|----|-------|---------------|
| 9  | phenyl | H, $NO_2$, H |
| 10 | 9-(10-nitroanthracene) | H, $NO_2$, H |
| 11 | m-terphenyl | H, H, H |
| 12 | H | H, $NO_2$, H |

*The salicylaldimine ring substituents shown were at the 4-, 5-, and 6-positions, respectively A. Synthesis of m-Terphenyl-Substituted Ligand in Chelate from Example 11

Preparation of 2-(α,α'-bisphenyl)-phenylphenol was carried out as described by the procedure of T. Satoh et al, Angew. Chem. Int. Ed. Engl. 1997, 36, 1740–1742. To a 300 mL Schlenk flask (in a nitrogen-filled dry box) containing a polytetrafluoroethylene stir bar were added 2-phenylphenol (6.85 g, 40.2 mmol), $PdCl_2$ (0.357 g, 2.01 mmol), and $CsCO_3$ (52.4 g, 161 mmol). The vessel was removed from the dry box and placed under an argon atmosphere. To the flask were added anhydrous DMF (200 mL) by cannula and iodobenzene (18 mL) by syringe. Subsequently, the reaction vessel was equipped with a reflux condenser and heated to 110° C. The orange colored solution quickly changed to a dark reddish-black colored mixture. The reaction was allowed to stir at 110° C. for 3 days. After the mixture was cooled to ambient temperature, it was acidified with 5M HCl. The acidic aqueous layer was extracted with ether, which was reduced in volume to give a red oil. Upon standing, crystals formed from the oily mixture. The crystalline product was collected on a frit and washed with hexane to provide pure product. The yield of 2-(α,α'-bisphenyl)-phenylphenol was 2.2 g (17 %). (Proton NMR ($CDCl_3$): δ 4.66 (s, 1H), 6.54 (dd, 1H, $J_{HH}$=8.3, 1.0 Hz), 6.58 (dt, 1H, $J_{HH}$=7.3, 1.0 Hz), 6.76 (dd, 1H, $J_{HH}$=7.3, 1.5 Hz), 6.94 (dt, 1H, $J_{HH}$=7.3, 1.5 Hz), 7.09–7.18 (m, 10H), 7.45–7.53 (m, 3H). Elemental analysis: (theoretical), C, 89.41%; H, 5.63%; (actual): C, 89.08%; H, 5.26%.).

The 2-(α,α'-bisphenyl)-phenylphenol was combined with 1.5 equivalents of dihydropyran, DHP (0.597 g, 7.10 mmol), $CH_2Cl_2$ (25 mL), and pyridinium p-toluenesulfonate (5 mg). The reaction mixture was allowed to stir at ambient temperature for 36 hours. Thereafter, the mixture was washed twice with water and dried over $Na_2SO_4$. Methylene chloride was removed under reduced pressure, and drying under vacuum removed unreacted DHP. The yield of THP-protected product was 1.75 g (92.3%). (Proton NMR ($CDCl_3$): 1.3–1.8 (m, 6H), 3.22–3.28 (m, 1H), 3.34–3.42 (m, 1H), 5.00 (s, 1H), 6.71 (dt, 1H, $J_{HH}$=7.4, 1.3 Hz), 6.88 (dd, 1H, $J_{HH}$=7.4, 1.5 Hz), 6.95 (d, 1H, $J_{HH}$=8.8 Hz), 7.06 (dt, 1H, $J_{HH}$=8.0, 1.4 Hz), 7.12–7.30 (m, 10H), 7.44–7.53 (m, 3H).).

The THP-protected 2-(α,α'-bisphenyl)-phenylphenol from above was placed in a dry vessel, degassed under vacuum and placed under an inert atmosphere. After addition of anhydrous ether (30 mL), the reaction vessel was chilled to –78° C., and n-butyllithium (2.56 mL, 4.10 mmol) was added dropwise over 5 minutes. The pale yellow solution was stirred at –78° C. for 5 minutes and allowed to gradually warm to ambient temperature. Upon warming, a white precipitate formed. The reaction mixture was allowed to stir at room temperature for 2.5 hours. After this time, the reaction vessel was cooled to –10° C. Anhydrous DMF (10 mL) was added dropwise over 5 minutes. Again, the reaction was allowed to stir at 0° C. for 5 minutes, warmed to room temperature and stirred for 1.5 to 2 hours. After this time, the reaction was quenched by slow addition of excess water. The ethereal layer was removed, washed twice with water, dried over $Na_2SO_4$, and solvent removed by rotary evaporation. Yield was 1.5 g (97.5%). (Proton NMR ($CDCl_3$): 1.34–1.78 (m, 6H), 3.16–3.22 (m, 1H), 3.42–3.56 (m, 1H), 4.70 (t, 1H, $J_{HH}$=1.5 Hz), 6.88 (t, 1H, $J_{HH}$=7.3 Hz), 7.02–7.20 (s broad, 12H), 7.50–7.64 (m, 3H), 10.05 (s, 1H).).

THP-protected 3-(α,α'-bisphenyl)-phenyl-2-hydroxybenzaldehyde (1.46 g, 3.36 mmol) from above was dissolved in ethanol (20 mL) and THF (15 mL) in a round bottom flask. To the flask was added a catalytic amount (5–10 mg) of pyridinium p-toluenesulfonate. The reaction was heated to 80° C. for two days. After this time, the solvents were removed under reduced pressure, and the crude product was recrystallized from ethyl acetate to yield a white solid (1.07 g, 91.0%) after drying. (Proton NMR ($CDCl_3$): δ 6.68 (t, 1H, $J_{HH}$=7.3 Hz), 7.04 (d, 1H, $J_{HH}$=1.5 Hz), 7.10–7.18 (s broad, 10H), 7.23–7.26 (m, 1H), 7.43 (d, 2H, $J_{HH}$=7.3 Hz), 7.50–7.56 (m, 1H), 9.68 (s, 1H), 10.91 (s, 1H).).

A 25 mL round bottom flask was charged with 3-(α,α'-bisphenyl)-phenyl-2-hydroxybenzaldehyde (0.500 g, 1.42 mmol) from above and 1.1 equivalents of 2,6-diisopropylaniline (0.277 g, 1.56 mmol). Methanol (18 mL) was added and the reaction mixture was heated to reflux. Upon dissolution, a catalytic amount (0.1 mL) of formic acid was injected by syringe. The reaction was allowed to reflux for an hour, at which point the methanol was removed by rotary evaporation. The Schiff base product was purified on a silica gel column with 70% hexanes/30% methylene chloride. The eluant was removed by rotary evaporation, providing a pale yellow solid (0.610 g, 85%) after drying under vacuum. Proton NMR ($CDCl_3$): δ 1.18 (d, 12H, $J_{HH}$=6.6 Hz), 2.82 (quintet, 2H, $J_{HH}$=7.3 Hz), 6.68 (t, 1H, $J_{HH}$=7.3 Hz), 6.98 (dd, 1H, 2.2 Hz), 7.11 (dd, 1H, $J_{HH}$=8.0, 1.4 Hz), 7.19–7.24 (m, 8H), 7.28–7.03 (m, 3H), 7.50–7.59 (m, 3H), 8.15 (s, 1H), 11.95 (br, 1H). $^{13}C$ NMR ($CDCl_3$): δ 23.73, 28.03, 117.68, 117.93, 123.17, 125.33, 126.18, 127.27, 127.44, 127.72, 128.91, 129.14, 129.34, 131.11, 134.60, 136.18, 138.65, 142.03, 142.75, 145.95, 158.79, 166.29. Elemental analysis: (theoretical) C: 87.19, H: 6.92, N: 2.75; (actual) C; 87.08, H, 6.88, N, 2.84.

B. Polymerizations

A Schlenk flask was charged with (tmeda)Ni($CH_3$)$_2$ (1.1 equiv. with respect to the ligand) in the dry box. A glass pressure bottle was charged with 60 μmol of ligand. The bottle and the Schlenk tube were removed from the dry box and degassed dry toluene (5 mL) was added under nitrogen by cannula to the flask. Degassed, dry toluene (85 mL) also was also added to the bottle containing the salicylaldimine ligand. The (tmeda) nickel reagent then was added to the ligand-containing solution by cannula. The resulting solution turned an orange-to-red color.

After stirring at room temperature for about 10 minutes, the glass reactor was pressurized to and maintained at 0.79 MPa (100 psig) for about 90 minutes with ethylene. Polymerization of the ethylene occurred during this time, and the temperature of the reaction solution rose significantly. At the end of an hour, the reactor was vented and the polymerization reaction terminated by addition of the mixture to acidified methanol. The polymer product precipitated in the methanol mixture and was collected by vacuum filtration and dried under reduced pressure.

After yield was calculated, catalyst productivity and selected properties of the polymer were determined. The results are shown below in Table III.

TABLE III

| Chelate (Ex. no.) | Yield (g) | $M_w$ ($10^3$) | $M_w/M_n$ | Activity (kg PE/mol Ni/hr) |
|---|---|---|---|---|
| 1 | 12.6 | 133 | 3.5 | 124 |
| 2 | 1.5 | ND | ND | 14.0 |
| 9 | 13.4 | 200 | 2.6 | 157 |
| 10 | 23.3 | 40 | 3.9 | 277 |
| 11 | 7.9 | 532 | 2.1 | ND |

ND = not determined

The data of Table III indicate that a complex according to the present invention may be formed in-situ to provide a useful catalyst for the polymerization of ethylene. With this type of in-situ method, the salicylaldimine ligand can contain an electron-withdrawing substituent (e.g., nitro).

A further experiment was performed to determine the nature of the catalytic species which was formed in-situ.

C. Nature of In-Situ Catalyst

In a dry box, the 3-phenylsalicylaldimine ligand (0.036 g, 0.09 mmol) and (tmeda)Ni(CH$_3$)$_2$ (0.021 g, 0.10 mmol) were weighed into a sample vial. Anhydrous deuterated acetonitrile (CD$_3$CN) was added to dissolve both compounds. A red-colored solution was obtained. After sitting overnight, the solution was divided into two approximately equal portions.

Proton NMR (CD$_3$CN, 300 MHz, 25° C.) of one portion revealed that the ligand had coordinated to the nickel quantitatively (i.e., no phenol OH proton was observed, and methyl shifts at δ −1.59, −1.25, −0.07 ppm (s, C$\underline{H}_3$Ni) corresponding to tetramethylethylenediamine and acetonitrile filling the labile coordination site).

The remaining portion of catalyst solution was added to a glass pressure bottle in a dry box. The assembled glass pressure reactor was removed from the dry box and degassed toluene (80 mL) was added. The reactor was pressurized and maintained at 0.79 MPa (100 psig) with ethylene. As ethylene was introduced, polymerization occurred. The reaction was allowed to proceed for 3 hours. Work up of the polymer product yielded polyethylene (1.5 g) after vacuum drying. M$_w$ was determined to be 25,650. The polydispersity (i.e., $M_w/M_n$) was 1.9.

Example 13

Copolymerization of Ethylene with Chelates Formed In-Situ

A series of polymerizations were carried out as follows:

In a dry box, a glass pressure bottle was charged with 60 μmol of a salicyialdimine ligand indicated in Table IV below under a nitrogen atmosphere. In similar fashion, a Schlenk flask was charged with (tmeda)Ni(CH$_3$)$_2$ (1.1 equiv. with respect to the ligand). The assembled glass pressure reactor and Schlenk flask were then removed from the dry box. The (tmeda)Ni(CH$_3$)$_2$ complex was dissolved in about 10 mL degassed toluene (added by cannula), while the ligand was dissolved in 80 mL degassed toluene (added by cannula). The desired amount of comonomer, ethyl 10-undecenoate, was added to the ligand solution.

The solution of (tmeda)Ni(CH$_3$)$_2$ was added by cannula to the ligand solution containing the comonomer. The resultant solution turned an orange-red color. After the solution was stirred for 5–10 minutes, the glass reactor was placed in a water bath (50° C.) and then pressurized with ethylene to a maximum pressure of 0.79 MPa (100 psig). The ensuing polymerization was allowed to proceed at the desired pressure for 1.5 hours.

After this time, the reaction vessel was vented, and the contents were poured in acidified methanol to precipitate white copolymer. The copolymer was isolated on a frit by filtration, washed and dried under vacuum. The yield as well as selected properties of the copolymer product were determined. The results are summarized below in Table IV.

TABLE IV

| Chelate (Ex. no.) | Amt. comonomer (equiv. relative to chelate) | $M_w$ ($10^3$) | $M_w/M_n$ | $T_m^b$ (° C.) | Mol % comonomer[a,c] |
|---|---|---|---|---|---|
| 9 | 700 | 96.4 | 3.3 | 117.9 | 0.5 |
| 10 | 700 | 69 | 2.2 | 122.4 | 1.0 |

[a]FTIR analysis: ester carbonyl stretch (C=O) at 1736 cm$^{-1}$.
[b]Copolymer melting point determined by differential scanning calorimetry at heating rate of 10° C./min.
[c]Copolymer composition determined by $^{13}$C NMR analysis.

Example 14

Polymerization in Presence of Polar Additive

The general procedure described in Example 13 was modified and used to demonstrate the polymerization of ethylene in the presence of a Lewis base additive using a neutral nickel(II) catalyst of the present invention which was formed in the presence of the additive by the in-situ method described previously.

Polymerizations were carried out with 60 μmol of ligand and 1.1 equivalents of (tmeda)Ni(CH$_3$)$_2$ in toluene (90 mL) at 0.79 MPa (100 psig) of ethylene. Reaction temperature was not controlled, and the polymerizations were allowed to continue for 1.5 hours.

The results are summarized in Table V below.

TABLE VI

| Chelate (Ex. no.) | Additive (equiv.) | Yield PE (g) | $M_w$ ($10^3$) | $M_w/M_n$ |
|---|---|---|---|---|
| 10 | diethyl ether (1500) | 1.6 | 66.0 | 6.7 |
| 10 | allylbutylether (1300) | 4.7 | 101.4 | 2.8 |
| 2 | acetonitrile (380) | 1.5 | 25.2 | 1.9 |

Various modifications and alterations that do not depart from the scope and spirit of this invention will become apparent to those skilled in the art. This invention is not to be unduly limited to the illustrative embodiments set forth herein.

We claim:

1. A process of forming a polymerization catalyst represented by the formulae:

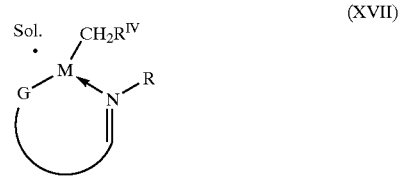

(XVII)

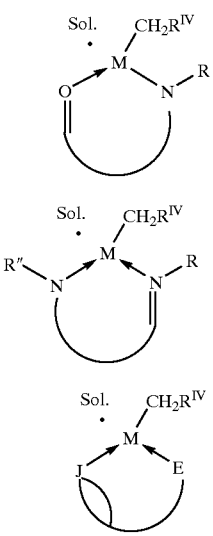

(XVIII)

(XIX)

(XXI)

wherein each R and R" independently represents a $C_4$–$C_{24}$ hydrocarbyl selected from the group consisting of an alkyl, a cycloalkyl, an aryl, an aralkyl, a substituted aryl having at least one position of the aromatic group substituted with a $C_1$–$C_{12}$ alkyl or a fused or unfused aryl group and a hydrocarbyl terminated oxyhydrocarbylene group;

G represents an oxygen or sulfur atom;

E represents an OH, SH, or NHR group;

J represents —O—, —N— or —S— as part of a ring structure;

$R^{VI}$ represents hydrogen, aryl, $Si(OR)_3$, or a tri($C_1$–$C_{12}$ hydrocarbyl)methyl group wherein each R is independently a $C_1$–$C_{12}$ hydrocarbyl;

U represents a hydrocarbylene group selected from the group consisting of arylene, arylalkylene, alkarylene, cycloalkylene, alkylene group, and mixtures thereof and wherein said group has carbon-carbon single covalent bonds only or combined with non-aromatic or aromatic carbon-carbon ethylenic double bonds within the hydrocarbylene group;

M represents a metal selected from the group consisting of Fe, Co, Ni, Ru, Rh, Pd, Os, Ir, and Pt; and Sol represents a polar solvent molecule:

comprising contacting a ligand compound free of electron-withdrawing groups which is selected from a compound represented by the general formulae:

(I)

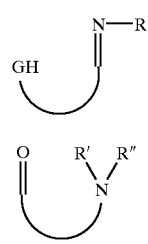

(II)

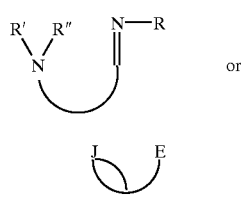

(III)

or (V)

wherein

R, G, E, J and U are as defined above; and each R' and R" independently is selected from hydrogen or an R group, as stated above, provided at least one R' and R" is a hydrogen:

with a di(tertiary amine) late transition metal reagent represented by the formula:

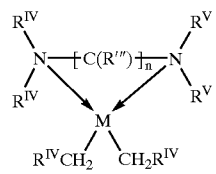

(XVI)

wherein

R'" represents hydrogen or a $C_1$–$C_5$ alkyl or substituted alkyl;

each $R^{IV}$ and $R^V$ independently represents a hydrocarbyl, or each $R^{IV}$ together and each $R^V$ together represents a hydrocarbylene group;

$R^{IV}$ is as defined above;

M is the above defined transition metal in the +2 oxidation state; and n represents an integer of from 0 to 3.

2. The process of claim 1 wherein the liquid and metal reagent are contacted in the presence of a polar liquid and a solid product is recovered.

3. The process of claim 2 wherein the polar liquid is an ether, a nitrile, an aldehyde, a ketone, an alcohol, an organic ester, a nitroalkane, a nitroaromatic or mixtures thereof.

4. The process of claim 2 wherein the polar liquid is acetonitrile, benzonitrile, tetrahydrofuran, pyridine or lutidine.

5. The process of claim 1 wherein the ligand and metal reagent are contacted in the presence of an olefinic monomer containing at least one hydrocarbyl group substituted thereon.

6. The process of claim 5 wherein the olefinic monomer is at least one 1-olefin, cycloolefin, functionalized 1-olefin or mixtures thereof.

7. The process of claim 1 wherein R is a cycloalkyl, an aryl, a substituted aryl having at least one position of the aromatic group substituted with a $C_1$–$C_4$ alkyl or a fused or unfused aryl group, or an oxyhydrocarbylene group;

R" is an R group;

G is an oxygen atom; and

J is an oxygen atom.

8. The process of claim 5, 6 or 7 wherein the ligand compound and the metal reagent are contacted in the presence of a polar liquid selected from the group consisting of an ether, a nitrile, an aldehyde, a ketone, an alcohol, an organic ester, a nitroalkane, a nitroaromatic and mixtures thereof.

9. A process of forming a polymerization catalyst represented by the formulae:

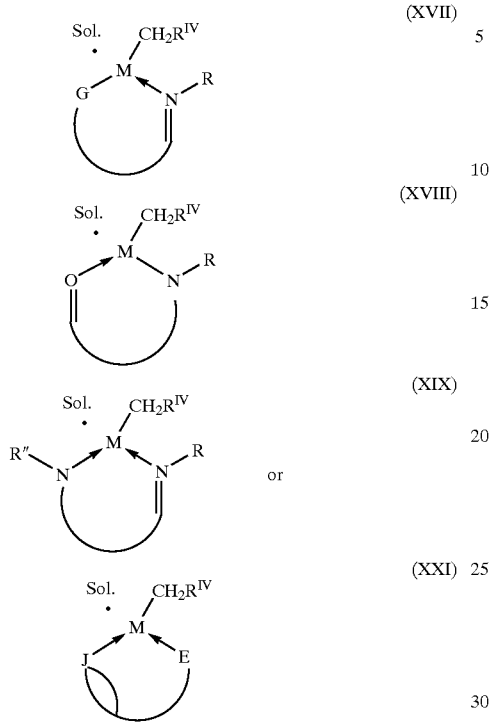

wherein each R and R" independently represents a $C_4$–$C_{24}$ hydrocarbyl selected from the group consisting of an alkyl, a cycloalkyl, an aryl, an aralkyl, a substituted aryl having at least one position of the aromatic group substituted with a $C_1$–$C_{12}$ alkyl or a fused or unfused aryl group and a hydrocarbyl terminated oxyhydrocarbylene group;

G represents an oxygen or sulfur atom;

E represents an OH, SH, or NHR group;

J represents —O—, —N— or —S— as part of a ring structure;

$R^{VI}$ represents hydrogen, aryl, $Si(OR)_3$, or a $tri(C_1$–$C_{12}$ hydrocarbyl)methyl group wherein each R is independently a $C_1$–$C_{12}$ hydrocarbyl;

U represents a hydrocarbylene group selected from the group consisting of arylene, arylalkylene, alkarylene, cycloalkylene, alkylene group, and mixtures thereof and wherein said group has carbon-carbon single covalent bonds only or combined with non-aromatic or aromatic carbon-carbon ethylenic double bonds within the hydrocarbylene group;

M represents a metal selected from the group consisting of Fe, Co, Ni, Ru, Rh, Pd, Os, Ir, and Pt; and Sol represents a polar solvent molecule:

comprising contacting, in a polymerization process zone, a compound represented by the general formulae:

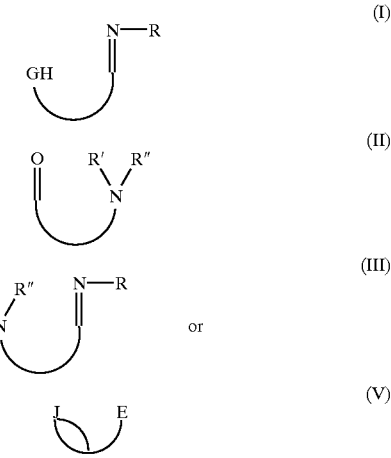

wherein
R, G, E, J and U are as defined above; and
each R' and R" independently is selected from the group consisting of hydrogen or an R group, as stated above, provided at least one R' and R" is a hydrogen:
with a late transition metal reagent represented by the formula:

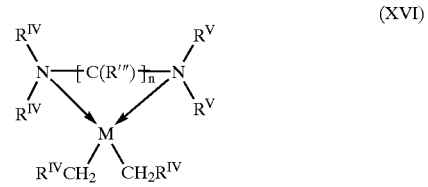

wherein
R'" represents hydrogen or a $C_1$–$C_5$ alkyl or substituted alkyl;
each $R^{IV}$ and $R^V$ independently represents a hydrocarbyl, or each $R^{IV}$ together and each $R^V$ together represents a hydrocarbylene group;
$R^{IV}$ is as defined above;
M is the above defined metal in the +2 oxidation state; and
n represents an integer of from 1 to 3.

10. The process of claim 9 wherein at least one of the R, R', R" or U groups of said ligand comprises an electron withdrawing group substituted hydrocarbyl.

11. The process of claim 9 wherein the ligand and metal reagent are contacted in a medium selected from the group consisting of olefinic monomer, inert organic compound and mixtures thereof.

12. The process of claim 10 wherein the ligand and metal reagent are contacted in a medium selected from the group consisting of olefinic monomer, inert organic compound and mixtures thereof.

13. The process of claim 9 wherein the ligand and metal reagent are contacted in the presence of a polar liquid.

14. The process of claim 10 wherein the ligand and metal reagent are contacted in the presence of a polar liquid.

15. The process of claim 13 wherein the polar liquid is an ether, a nitrile, an aldehyde, a ketone, an alcohol, an organic ester, a nitroalkane, a nitroaromatic or mixtures thereof.

16. The process of claim 14 wherein the polar liquid is an ether, a nitrile, an aldehyde, a ketone, an alcohol, an organic ester, a nitroalkane, a nitroaromatic or mixtures thereof.

17. The process of claim 15 wherein the polar liquid is acetonitrile, benzonitrile, tetrahydrofuran, pyridine or lutidine.

18. The process of claim 16 wherein the polar liquid is acetonitrile, benzonitrile, tetrahydrofuran, pyridine or lutidine.

19. The process of claim 9 wherein the ligand and metal reagent are contacted in the presence of an olefinic monomer containing at least one hydrocarbyl group substituted thereon.

20. The process of claim 19 wherein the olefinic monomer is at least one 1-olefin, cycloolefin, functionalized 1-olefin or mixtures thereof.

21. The process of claim 9 wherein R is a cycloalkyl, an aryl, a substituted aryl having at least one position of the aromatic group substituted with a $C_1$–$C_4$ alkyl or a fused or. unfused aryl group, or an oxyhydrocarbylene group;

R" is an R group;

G is an oxygen atom; and

J is an oxygen atom.

22. The process of claim 9, 10, 13, 14, 19, 20, or 21 wherein at least one of the compounds (I), (III), (IV) and (V) and the metal reagent are contacted in the presence of a polar liquid selected from the group consisting of an ether, a nitrile, an aldehyde, a ketone, an alcohol, an organic ester, a nitroalkane, a nitroaromatic and mixtures thereof.

* * * * *